(12) United States Patent
Webb

(10) Patent No.: US 6,644,322 B2
(45) Date of Patent: Nov. 11, 2003

(54) HUMAN LANGUAGE TRANSLATION OF PATIENT SESSION INFORMATION FROM IMPLANTABLE MEDICAL DEVICES

(75) Inventor: James D. Webb, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 299 days.

(21) Appl. No.: 09/887,376

(22) Filed: Jun. 22, 2001

(65) Prior Publication Data

US 2002/0023654 A1 Feb. 28, 2002

Related U.S. Application Data

(60) Provisional application No. 60/213,859, filed on Jun. 23, 2000.

(51) Int. Cl.[7] ............................................... A61B 19/00
(52) U.S. Cl. ...................... 128/899; 600/300; 607/30; 715/513; 715/523
(58) Field of Search .................. 128/899, 903, 128/904; 600/300, 508, 509, 510, 522, 523; 607/30, 32, 59, 60; 707/102, 103; 709/201, 203, 206, 217, 246; 715/500.1, 513, 517, 522, 523

(56) References Cited

U.S. PATENT DOCUMENTS

| | | |
|---|---|---|
| 5,188,105 A | 2/1993 | Keimel ........................... 607/5 |
| 5,330,513 A | 7/1994 | Nichols et al. ............... 607/32 |

(List continued on next page.)

FOREIGN PATENT DOCUMENTS

| | | |
|---|---|---|
| WO | 9914882 | 3/1999 |
| WO | 9941682 | 8/1999 |
| WO | 0070529 | 11/2000 |

OTHER PUBLICATIONS

Adler et al "Extensible Stylesheet Language" XSL Nov. 2000.

(List continued on next page.)

*Primary Examiner*—Willis R. Wolfe
(74) *Attorney, Agent, or Firm*—Girma Wolde-Michael

(57) ABSTRACT

A system and method for efficiently and relatively inexpensively providing a capability of translating "Patient Session Information" comprising IMD data and patient data stored in IMD memory in one human language and optionally other patient data from other sources into another human language. The local language translation is effected by first employing an Extensible Mark-up Language (XML) converter for converting Patient Session Information from an initial format, such as a memory dump format, ASCII format, a waveform format, a numeric format, or a binary format, to an XML format, thereby providing XML formatted Patient Session Information. Then, the XML formatted Patient Session Information is subjected to transformation by a human language specific Extensible Stylesheet Language (XSL) stylesheet into XSL transformed Patient Session Information. The XSL stylesheet effects translation of the XML formatted Patient Session Information into a language understandable to the user in an HTML format or another XML format or another suitable format, e.g., PDF or SVG graphic image formats. The XSL transformed Patient Session Information is thereby rendered understandable to the user that selects the human language when the translated Patient Session Information is delivered as by visual display or print-out or audible presentation or storage depending upon a selection of the user. The translated Patient Session Information can be stored in the programmer memory or in the IMD memory or transferred or exported to another device or system interconnected with the programmer including a remote server accessed through the Internet.

48 Claims, 9 Drawing Sheets

U.S. PATENT DOCUMENTS

| | | | |
|---|---|---|---|
| 5,331,966 A | | 7/1994 | Bennett et al. ............. 600/508 |
| 5,345,362 A | | 9/1994 | Winkler ...................... 361/681 |
| 5,350,411 A | | 9/1994 | Ryan et al. .................... 607/32 |
| 5,372,607 A | | 12/1994 | Stone et al. .................. 607/30 |
| 5,544,661 A | | 8/1996 | Davis et al. ................ 600/513 |
| 5,564,434 A | | 10/1996 | Halperin et al. ............ 600/488 |
| 5,693,076 A | | 12/1997 | Kaemmerer ................. 607/59 |
| 5,752,976 A | | 5/1998 | Duffin et al. ................. 607/32 |
| 5,800,465 A | | 9/1998 | Thompson et al. ............ 607/9 |
| 5,817,137 A | * | 10/1998 | Kaemmerer ................. 607/30 |
| 5,833,623 A | * | 11/1998 | Mann et al. .................. 607/32 |
| 5,997,476 A | | 12/1999 | Brown ....................... 600/300 |
| 6,083,248 A | | 7/2000 | Thompson ................... 607/30 |
| 6,121,963 A | * | 9/2000 | Ange ...................... 715/500.1 |
| 6,249,703 B1 | * | 6/2001 | Stanton et al. ................ 607/30 |
| 6,250,309 B1 | * | 6/2001 | Krichen et al. ............. 128/899 |
| 6,440,068 B1 | * | 8/2002 | Brown et al. ............... 600/300 |
| 6,442,430 B1 | * | 8/2002 | Ferek-Petric ................. 607/32 |
| 6,453,329 B1 | * | 9/2002 | Dodgen ...................... 715/516 |
| 6,466,940 B1 | * | 10/2002 | Mills .......................... 707/102 |
| 6,473,638 B2 | * | 10/2002 | Ferek-Petric ............... 600/523 |
| 6,480,745 B2 | * | 11/2002 | Nelson et al. ................ 607/60 |
| 6,532,473 B2 | * | 3/2003 | Niazi et al. ............. 707/103 X |
| 2002/0032720 A1 | * | 3/2002 | Nelson et al. .............. 709/201 |

OTHER PUBLICATIONS

James Clark "Associating Style Sheets with XML Documents" Jun. 1999.

Lie et al "Cascading Style Sheets, Level 1" Jan. 1999.

* cited by examiner

HUMAN LANGUAGE TRANSLATION OF PATIENT SESSION INFORMATION FROM IMPLANTABLE MEDICAL DEVICES

This application claims priority from Provisional Application No. 60/213,859 filed Jun. 23, 2000.

CROSS-REFERENCE TO RELATED APPLICATION

Reference is hereby made to commonly assigned co-pending U.S. patent application Ser. No. 09/358,081 filed Jul. 21, 1999, for A SYSTEM AND METHOD FOR TRANSFERRING INFORMATION RELATING TO AN IMPLANTABLE MEDICAL DEVICE TO A REMOTE LOCATION in the names of Jack P. Krichen and James David Webb 1. Field of the Invention The present invention relates to a system for retrieving stored Patient Session Information from an implantable medical device (IMD), and more particularly to such a system formatting the Patient Session Information in an XML format enabling translation of the XML formatted Patient Session Information into a human language understandable to a health care provider through the use of human language stylesheets applied to the XML formatted Patient Session Information.

2. Background of the Invention

Many types of IMDs have been developed for monitoring a medical condition and/or providing a therapy to a patient over the years. Such IMDs include electrical stimulation devices for stimulating body organs and tissue to evoke a response for enhancing a body function or to control pain and drug delivery devices for releasing a drug bolus at a selected site. Other more passive IMDs have been developed for simply monitoring a patient's condition.

Chronically implanted cardiovascular IMDs for monitoring cardiovascular conditions and providing therapies for treating cardiac arrhythmias have vastly improved patient's quality of life as well as reduced mortality in patient's susceptible to sudden death due to intractable, life threatening tachyarrhythmias. Patients are allowed the freedom from hospital or home confinement or bed rest as IMD technology has grown more sophisticated with capabilities to diagnose and treat a greater range of patient conditions, including otherwise life threatening conditions. The resulting improved patient mobility is a quality of life rationale for implanting such IMDs. However, the improved mobility brings with it the need to maintain the ability to communicate with the IMD for a variety of reasons.

Early in the development of cardiac pacemakers, patient follow-up to monitor pacemaker operation was facilitated by telephonic transmissions of skin surface ECGs in real time to a physician's office employing such systems as the MEDTRONIC® TeleTrace® ECG transmitter. Over time, various patient worn, ambulatory ECG and device monitors have been developed for providing ECG data for analysis of cardiac arrhythmias. At the same time, IMDs were designed to be programmable in operating mode and parameters employing "telemetry" transceivers in the IMD and an external programmer.

In the case of current technology arrhythmia control devices, e.g. multi-programmable, cardiac pacemakers and implantable-cardioverter-defibrillators (ICDs), a relatively wide range of device operating modes and parameters are remotely programmable to condition the device to diagnose one or more cardiac arrhythmias and deliver an appropriate therapy. In cardiac pacemakers, the pacing rate in one or both heart chambers is governed by algorithms that process the underlying cardiac rhythm as well as physiologic conditions, e.g. patient activity level and other measured variables, to arrive at a suitable pacing rate. The pacemaker operating modes and the algorithm for establishing the appropriate pacing rate are programmed into internal memory by accessing the implanted pacemaker's telemetry transceiver with an external programmer during a downlink telemetry transmission. Similarly, with ICDs, the diagnosis of a tachyarrhythmia requiring delivery of a treatment therapy and the therapies to be delivered are governed by operating modes and algorithm parameters that may be programmed into device memory using such a programmer.

Moreover, such IMDs have the capability to process the patient's electrogram (EGM) and any measured physiological conditions employed in the diagnosis and to store the data, particularly such data that is related to a detected arrhythmic episode satisfying the criteria for treatment, for subsequent telemetry out or uplink telemetry on interrogation of the device memory by the external programmer. For example, the Medtronic® CHRONICLE® IHM implantable heart monitor senses blood pressure within a heart chamber and the EGM of the heart using an EGM and pressure sensing lead of the type disclosed in commonly assigned U.S. Pat. No. 5,564,434. Such implantable monitors when implanted in patients suffering from cardiac arrhythmias or heart failure accumulate date and time stamped data that can be of use in determining the condition of the heart over an extended period of time and while the patient is engaged in daily activities. The telemetered out data is analyzed and may be employed to establish or refine the operating modes and parameters of the device operating algorithms by reprogramming in the corresponding operating mode or parameter data.

A wide variety of programming and interrogation techniques have been devised over the years. When programming techniques were first devised, the paramount concerns addressed related to patient safety. Safeguards were built in to address the concern that the patient could be put at risk of inadvertent mis-programming of the IMD, e.g. programming too high a rate for a pacemaker or programming the pacing or sensing functions off, by stray electromagnetic fields. For this reason, and in order to avoid high current consumption that would shorten the IMD life, telemetry operating range was extremely limited. In systems continuing to the present time, downlink telemetry has required application of a magnetic field at the patient's skin over the IMD to close a reed switch while RF programming or interrogating commands are generated to be received by the IMD transceiver. The programming or interrogating commands are decoded and stored in memory or used to trigger uplink telemetry of stored data and operating modes and parameters by the IMD transceiver.

Examples of such medical device programmers include the Medtronic® Model 9760 pacemaker programmer and the Model 9790 universal programmer for bradycardia pacemakers and tachyarrhythmia devices described in U.S. Pat. Nos. 5,372,607, 5,345,362, and 5,350,411.

As mentioned above, one of the rationales and attributes of IMDs of the type described is that the patient is allowed to be ambulatory while his/her medical condition is monitored and/or treated by the IMD. As a safety precaution, programmers capable of programming all the operating modes or functions of the IMD and for initiating interrogation through the telemetry system are generally not provided to the patients. Patients are periodically examined and device interrogation is conducted by the physician using the external programmer during scheduled follow-up visits to the physician's office or clinic. This limits the frequency of monitoring and may require certain patients to remain within easy reach of the physician's office in case of an emergency.

Such emergency conditions, e.g. device failure to deliver a therapy when required, physiologic variable changes resulting in inability of the device to effectively treat the patient, accidents unrelated to the patient's condition being treated, other illnesses or transient problems, etc., may arise unexpectedly and cause a patient to require treatment by a physician unfamiliar with the IMD or the patient's medical history. Perhaps, for this reason or simply for convenience, it has been proposed in the above-referenced '380 patent to store patient data (listed in Table V thereof) in memory in the IMD that can be interrogated and retrieved by telemetry using a compatible programmer. The '380 patent also describes other types of stored data and the storage of operating and control algorithms in bytes in RAM. A comprehensive listing of data stored in memory in a rate-responsive cardiac pacemaker also appears in U.S. Pat. No. 5,330,513 also incorporated herein by reference in its entirety.

Patients traveling domestically or in a foreign country typically do not carry their medical records with them, although they are instructed to carry identification of the IMD and any medications they are taking. Patients are also typically not fully cognizant of their medical records or able to recite past treatments that may or may not have been effective, medications they are allergic to, and the like. If an emergency arises, and the cause and treatment is not apparent to the medical personnel consulted, then it may be necessary to consult with the patient's primary care physician and await receipt of the patient's medical records before effective treatment can be commenced. Thus, it would be useful to store patient data in the medical device implanted in the patient for retrieval under either routine follow-up or under emergency conditions.

Most IMDs utilize various formats, such as waveform encoding formats, numeric formats, binary formats, and the American Standard Code for Information Interchange (ASCII) format, which is a specification for seven-bit patterns used to represent printable characters and controls (such as a carriage return) used for data communication between microprocessors or computers. ASCII and binary formats are common formats used in the medical device industry.

Despite the general desire to do so, the storage of patient data in the limited memory available in such IMDs has not been pursued to any extent because it can consume too many memory bytes that otherwise are considered to be better used to store diagnostic history data and device therapy delivery history data accumulated and stored by the medical device over time as described in the '513 patent and in the above-referenced '607 patent. With increasing memory capacities, future IMDs could also store patient data. However, the straightforward approach of storing ASCII text in the medical device is an unacceptable strategy. It would be too tedious for the physician to type in patient histories and too time-consuming to telemeter the full text out.

The programmers must function in a human language that is understandable to the user to compose programming commands for programming the operating modes and parameter values of the IMD and to compose patient and IMD data to be stored in IMD memory in a telemetry session. The user must also be able to initiate uplink telemetry transmission of patient data that was previously stored in IMD memory as well as stored IMD data and physiologic data collected in real-time.

While English is widely used and understood by the medical community around the world, it is still necessary to provide programmers that display such data and programmer commands in the prevailing local language of the country or even a region of a country so they can be used as described above. Thus, it is necessary to provide specific language programmers for use in such countries or regions. Currently, the prevailing way of providing such languages is through a removable storage medium, e.g., floppy disks or CD-ROMs that provide the software written in the local language that the programmer is expected to function using. Current programmers are also designed to be continually updated with new features or to program and interrogate each newly introduced IMD type or model through rewritten software that is distributed worldwide as floppy disks or CD-ROMs or memory cards to the owners of the programmers so that the software can be upgraded. The software is typically written in conventional programming languages. The translations of the software into all the prevailing human languages are time consuming and therefore quite expensive, particularly as it is necessary to continually provide the upgrades for newly introduced IMDs. As a result, short cuts are also often introduced wherein more commonly understood terms may be stated in English and other expressions are in the local language, which could conceivably confuse some users of the programmers.

Moreover, a user may not have a programmer that is capable of operating with an IMD in a patient from another country or region to receive and display or print out patient data and IMD data that is stored in IMD memory in a human language differing from the software resident in the programmer.

Commonly assigned U.S. Pat. No. 5,693,076 discloses a system and method of operation thereof for storing patient related data within an IMD and retrieving and regenerating the patient related data using a generative grammar and graphic user-interface software in a programmer having uplink and downlink telemetry capabilities. A generative grammar resident in the programmer is selected, and it prompts a physician or other user to enter patient specific variables by selecting menu choices or making data entries in data entry fields which generated by grammar rules while constructing a textual narrative report about the patient in a human language. Simultaneously, in the programmer, a digital patient related data bit string is assembled that identifies the generative grammar and encodes the choices and values as they are entered by the physician. Also simultaneously, internal computer records of the patient related data are stored in computer memory. The generative grammar invokes text and menus or data entry fields for the continuing narrative that depend upon the preceding narrative in a grammatically correct manner. When the narrative is completed, the simultaneously generated bit string is stored in the IMD using conventional downlink telemetry transmission protocols.

As disclosed therein, a generative grammar resident in the programmer is selected, and by following that generative grammar, a software algorithm in the programmer prompts a physician to enter information by selecting menu choices or making data entries in data entry fields. These choices and values are used within the framework of the grammar rules comprising the grammar to construct a textual narrative about a patient in a human language. In the programmer, a digital bit string is assembled that identifies the generative grammar and encodes the choices and values as they are entered by the physician into a patient related data bit string. Simultaneously, the corresponding textual narrative is composed and displayed for the physician, and an internal computer record of patient related data is maintained. The physician's entries invoke text and menus or data entry fields for the continuing narrative that depend upon the preceding narrative in a grammatically correct manner. When the narrative is completed, the resulting patient related data bit string is stored in the IMD using conventional downlink telemetry. The amount of IMD memory used in storing the patient related data bit string is minimized. Only the size of the generative grammar determines what can be expressed by the physician about the patient and stored in the IMD memory.

At a later time, the bit string stored in IMD memory can be uplink telemetry transmitted to the external programmer on command and decoded to identify the generative grammar. The regenerating process involves using the programmer-resident generative grammar to reconstruct the narrative and display it in the human language of the programmer-resident grammar in textual narrative form and to extract defined data for display in alternative tabular form. The external programmer then uses the generative grammar to regenerate the textual narrative for display and/or printing. Thus, the textual narrative patient related data from the patient related data bit string is regenerated in any selected human language for which there exists a formal generative grammar that is correlated to the original formal generative grammar used to enter and store the patient related data in IMD memory.

Advantageously, the patient related bit string can be efficiently downlink telemetry transmitted into a minimal amount of memory of an IMD because it typically is an order of magnitude more compact than the narrative text it encodes. Storage of only the patient name, patient specific variables, including menu choices and alphanumeric data, allows paragraphs of regenerable text (several kilobytes in size) to be downlink telemetry transmitted and stored in the IMD as several hundred bits. Only the comprehensiveness of the generative grammar, and not the amount of memory in the IMD or the software in the programmer, determines what can be expressed by the physician about the patient, encoded as a bit string and stored in the IMD.

It is therefore possible to provide physicians with a means of composing and storing textual information about a patient's medical history, medications, rationale for treatment, etc., in his/her IMD without requiring extensive typing or lengthy telemetry times. This information is then available to any physician with access to a programmer with the appropriate programmer-resident generative grammars, whenever the IMD memory is interrogated, regardless of where the patient travels. The generative grammar-based approach to patient data storage as described above is independent of the architecture, telemetry speed, and memory format of the IMD.

The system of the '076 patent relies upon the provision of the generative grammar in multiple human languages so that a physician or other health care provider can select a native language to operate the system in. Thus, all of the possible human languages must be created and stored in programmer memory or in a floppy disk, a memory card, or a CD-ROM or the like as described above. While it is suggested that the patient data received from the IMD can be regenerated and displayed in any language of choice, there is no specific disclosure of how this would be done. Presumably, the programmer would have to associate the patient related data bit stream to the appropriate grammar in the selected language, and the display or printout would be in that language.

As patient population, medical knowledge, and IMD technology expand exponentially, costs also increase such that considerable efforts are brought to bear to make the provision of health care far more efficient and cost effective. A wide variety of initiatives have been undertaken to control costs. Substantial increases in productivity and quality have been associated with the computerization of the work place and the proliferation of information technologies that involve transmission of information between computers leading to a lowering of costs in many industries. Multiple types or combination of network architectures have been put into place, including community access television (CATV) networks, the public switched telephone network (PSTN), the integrated services digital network (ISDN), the Internet, local area networks (LAN), wide area networks (WAN), wireless communications networks, asynchronous transfer mode (ATM) networks, etc, to facilitate such data transmission. Software and hardware developments have also increased the computing and data transmission capabilities of servers, computer workstations, personal computers, and the ever-increasing variety of other peripheral devices capable of accessing a network leading to "pervasive computing".

One popular technology enjoying wide use with the Internet is known as the Worldwide web. The Worldwide web enables a computer to locate a remote server using the domain name service (DNS) and then establish a connection to the server and retrieve information using a communication protocol called the Hypertext Transfer Protocol (HTTP). Each item of information available using the Web, including files, images, or pages, is called a resource. A Uniform Resource Locator (URL) uniquely identifies each resource stored on a server. A URL is a form of network address comprising a domain name coupled to an identifier of the location of information stored in a network.

The local computer requests information by providing a request containing a URL of the desired information to the remote server. The server receives the request, locates the page of information corresponding to the URL, and returns the page to the local computer over the HTTP connection. The pages of information are files prepared in the Hypertext Markup Language (HTML). The local computer runs a browser program that can read HTML files, interpret HTML codes in the files, and generate a complex graphical display.

These developments are being brought to bear in the effort to control the costs of medical and health care, particularly of patients who are not confined to a health care facility, in a wide variety of ways. Over the years, many systems have been advanced for remote monitoring of patients through radio or telephone communication or "telemedicine" links as disclosed, for example, in U.S. Pat. No. 5,544,661. More recently, systems for effecting interactive communication and remote monitoring of ambulatory patients have been proposed employing Internet based information technologies as disclosed in U.S. Pat. No. 5,997,476 and in PCT Publication Nos. WO 99/14882 and WO 99/41682, for example. Various systems have been proposed to provide medical information and assistance to patient subscribers to Internet based services as disclosed in PCT Publication No. WO 00/70529, for example.

Advances in computing and information technologies have also been contributed to the design and manufacture of the above-described IMDs and programmers. Virtually all IMDs and external programmers providing the telemetry capability have a microcomputer-based architecture. Current programmers are virtual personal computers, lacking only some of the capabilities of interacting with peripheral devices commonly used with personal computers. These advances have enabled the above-described proliferation of types of IMDs and advancement in their capabilities while tending to not increase their costs.

It has been recognized that there is a need to reduce the cost of conducting telemetry sessions that are borne by the medical care provider and imposed on the patient in terms of lost work time. Moreover, it has been recognized that the information technologies and available networks introduce the possibility of continuously monitoring IMDs wherever the IMD bearing patient may happen to be at any given time as set forth, for example, in commonly assigned U.S. Pat. Nos. 5,752,976 and 6,083,248.

Thus, a number of proposals have been advanced to facilitate conducting telemetry sessions with IMDs virtually automatically employing information technologies and available networks of the types listed above. Typically, a central database and communications center is manned by a staff that initiates a remote telemetry session and oversees the collection of the data and analyzes it. For example, it has been proposed in the above-referenced '011 patent that a wide variety of patient data be automatically collected from an IMD in a patient, transmitted over an available network to a remote center, and maintained in a patient care record in a centralized database at the center. Baseline and updated patient data are maintained in the patient care record by a database server. The patient data is manipulated to make a determination of patient "wellness".

As a result of all of these considerations and developments, there is a need to provide a way of communicating and understanding all such patient data and IMD data in a local human language no matter the language that the data is originally stored in. There is a need to increase the speed of development and to reduce the costs of developing and distributing effective translation tools to perform such translations of such data resident in memory of any IMD, external programmer, external patient monitor, local personal computer, or a remote database of a remote computer or mainframe.

There is also a need for a system that will permit specific desired information to be transferred to a location remote from the IMD in a format that can easily be interpreted, manipulated and translated into a desired human language.

SUMMARY OF THE INVENTION

The present invention therefore provides a system and method for efficiently and relatively inexpensively providing a capability of translating "Patient Session Information" comprising IMD data and patient data stored in IMD memory in one human language and optionally other patient data from other sources into another human language. The local language translation is effected by first employing an Extensible Mark-up Language (XML) converter for converting Patient Session Information from an initial format, such as a memory dump format, ASCII format, a waveform format, a numeric format, or a binary format, to an XML format, thereby providing XML formatted Patient Session Information. Then, the XML formatted Patient Session Information is subjected to transformation by a human language specific stylesheet, e.g., an Extensible Stylesheet Language (XSL) stylesheet, into translated Patient Session Information understandable to the user. The stylesheet effects translation of the XML formatted Patient Session Information into a language understandable to the user in an HTML format or another XML format or another suitable format, e.g., PDF or SVG graphic image formats. The XSL transformed Patient Session Information is thereby rendered understandable to the user that selects the human language when the translated Patient Session Information is delivered as by visual display or print-out or audible presentation or storage depending upon a selection of the user. The translated Patient Session Information can be stored in the programmer memory or in the IMD memory or transferred or exported to another device or system interconnected with the programmer including a remote server accessed through the Internet.

A user can employ a programmer in a contemporaneous telemetry session with the IMD to retrieve Patient Session Information and to transform it into a human language understandable to the user. Or the user uses a local computer either in a connection with programmer in a contemporaneous telemetry session with the IMD or to access stored Patient Session Information relating to an earlier telemetry session and to transform it into a human language understandable to the user. Or the user uses the local computer to access Patient Session Information stored on a remote database of a data center or server through an Internet connection or an Intranet connection or the like and to transform it into a human language understandable to the user that is displayed or printed from the local computer. In this case, the local computer may be remote from the patient, e.g., in a physician's office, and not coupled to the programmer in any way except possibly through the Internet connections.

In a one exemplary variation of the present invention, the XML converter and the XSL stylesheet are installed in the programmer so that the above-described functions are performed using the programmer. The XSL transformed Patient Session Information can be transferred to a local computer directly or indirectly coupled to the programmer or to a remote computer or data center or server accessible through an Internet connection.

In a further exemplary variation particular to an external patient monitor and a local computer, the uplink telemetry transmitted Patient Session Information received by the external patient monitor is transferred to the local computer. The transferred Patient Session Information is formatted into XML formatted Patient Session Information in the local computer.

In a still further exemplary variation of the present invention, the XML formatted Patient Session Information is formatted either in the programmer or in an external patient monitor that receives uplink telemetry transmissions from the IMD when the patient is in the vicinity and other conditions are met. Or the Patient Session Information is formatted in the IMD itself so that XML formatted Patient Session Information is uplink telemetry transmitted to the programmer or external patient monitor. The XML formatted Patient Session Information is then transferred in any of the known manner to a local computer directly or indirectly coupled to the programmer or external patient monitor or to a remote computer or data center through an Intranet or Internet connection or any of the above-listed and any other known data transfer mechanisms.

In these cases, the XML formatted Patient Session Information can be permanently or temporarily stored in memory at the local computer or remote computer or a database of a data center or server accessed via the worldwide web. The XML formatted Patient Session Information can be accessed by a user at the time of transfer or later in time and rendered understandable to the user who selects the human language XSL stylesheet of his/her choice.

The present invention works with standard communications modules, such as a transmission control protocol/Internet protocol (TCP/IP) module, located at both the location of the IMD and at a remote location. Thus, a feature of the present invention is the ability to transfer XSL transformed Patient Session Information and XML formatted Patient Session Information over most communication modules between any of the external devices via an Internet connection. The selection of the human language XSL style sheet to effect the transformation can be effected automatically through recognition of the human language that the computer operating system or web browser is set to when the user seeks to access XML formatted Patient Session Information.

The present invention is compatible with various presently used and proposed external medical devices that cooperatively collect and exchange Patient Session Information stored in IMD memory or developed in real time by the IMD and uplink telemetry transmitted to the external medical device. These external medical devices include programmers, external patient monitors, cell phones, personal digital assistants (PDAs), specialized smart cards in home computers, etc., that at least can receive uplink telemetry transmitted Patient Session Information and can be used to provide one or more of displaying, storing, printing, transferring or audibly stating the Patient Session Information in any selected language. Preferably, such external medical devices receive and transmit information over networks including local area networks or the Internet and run other complex programs. Preferably, such external medical devices can transmit the XML formatted Patient Session Information through the worldwide web to remote servers and databases.

The stylesheets that transform XML formatted Patient Session Information into any format and language increase the flexibility of accessing the Patient Session Information resident either at the programmer, external patient monitor, local computer, remote computer, etc.

The writing of stylesheets, e.g., XSL stylesheets, for all desired human languages is much easier than writing language translation software, and therefore can be completed faster at much less cost. The XSL stylesheets can be easily installed on a web server and can be accessed through a web browser for use at the site or downloading to a user's personal computer and installation in the programmer. In HTML displays, the user is presented with a display of the XSL stylesheet button that can be selected to apply the language translation. Or, the XSL stylesheet can be automatically retrieved and applied by detecting the human language set for computer operating system or web browser.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
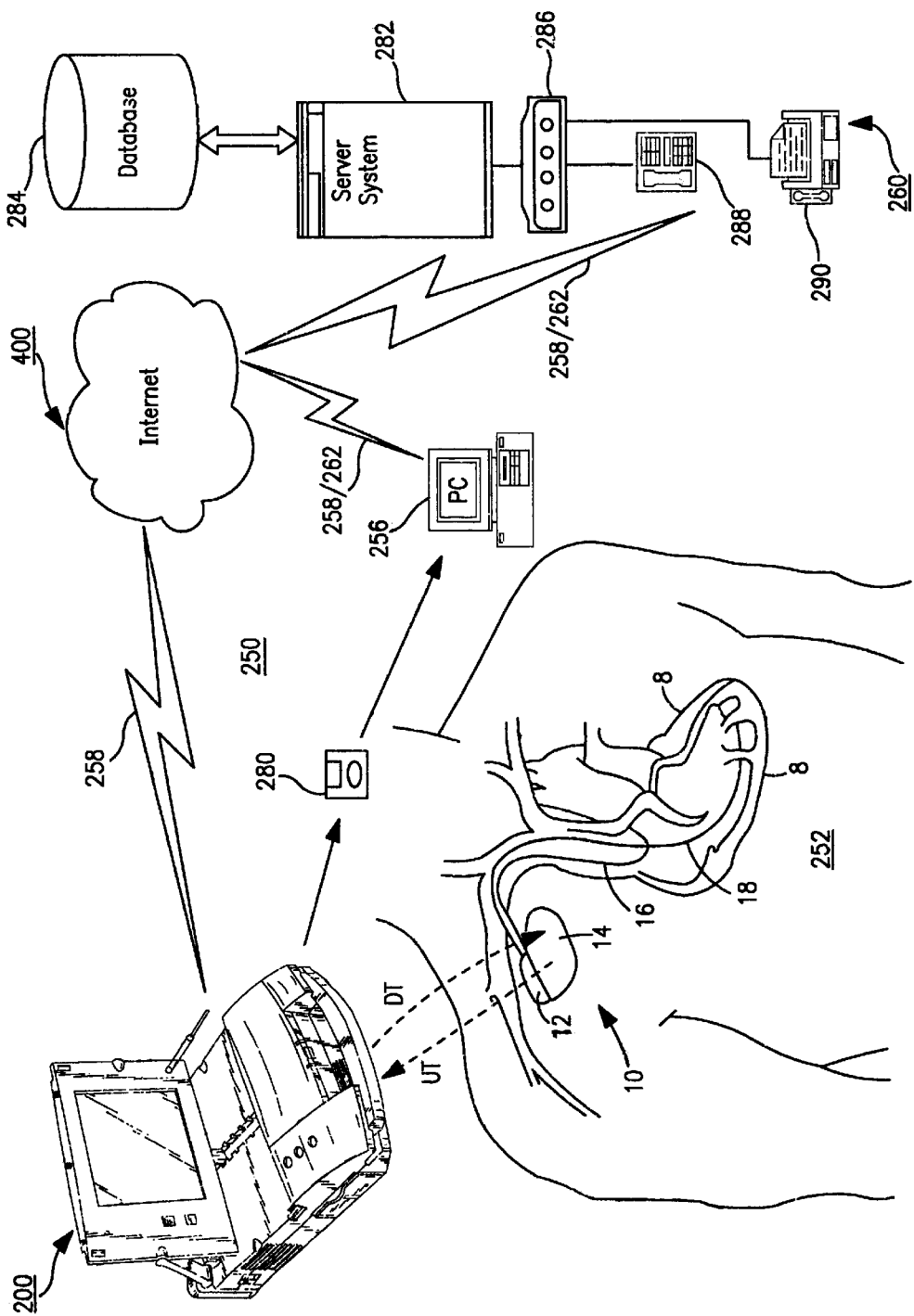
FIG. 1 is a simplified schematic view of one embodiment of an IMD comprising a monitor or IPG coupled with a lead extending into the right ventricle associated with a programmer, a computer and a remote computer and associated peripherals in a system of the present invention.

In the following detailed description of the preferred embodiments, reference is made to the accompanying drawings that form a part hereof and that illustrate specific preferred embodiments of practicing the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention provides a system and method for efficiently and relatively inexpensively providing a capability of translating Patient Session Information comprising IMD data and patient data stored in IMD memory in one human language and optionally other patient data from other sources into another human language. The local language translation is effected by first employing an XML converter for converting Patient Session Information from an initial format, such as a memory dump format, ASCII format, a waveform format, a numeric format, or a binary format, to an XML format, thereby providing XML formatted Patient Session Information.

XML is a language-definition promoted by Microsoft Corporation and Netscape Communications Corporation in which information elements are bracketed by complementary tags ("<xml>,</xml>") that indicate that the bracketed information element is in the XML grammar. XML arose out of standard generalized markup language (SGML) and HTML standards efforts.

HTML is a tag-based ASCII language that is used to specify the content and hypertext links to other documents on worldwide web servers on the Internet. Browsers can then be used to view the prepared documents and follow links to display other documents. HTML is a structured language that cannot be modified to suit a specific need. Since HTML relies on predefined tags and attributes, there is no control over the structure of data in a HTML document. Thus, while HTML works sufficiently for a text document, it is not compatible with creating a unique format, such as those needed for non-text data including EGM tracings and the like.

The XML language supports the UNICODE character-encoding standard so that the bracketed information can be expressed in any human language. While HTML has predefined tags, XML can be used to define tags as defined. The common mantra of XML is that it separates content from presentation which is a major difference from HTML. A user can employ XML to direct a markup language to, in effect, define in-house data handling methods. It allows a user to "normalize" varied data input sources to allow complex data handling. XML allows a user to change the definitions of tags as the process evolves. In addition, XML provides embedded structure, which replaces the order and layout of previous mark-up languages, such as SGML and HTML. XML also provides easy validation through the use of Data Type Definition (DTDs) with validating parsers.

Since XML does not rely on predefined tags and attributes, a user has complete control over the structure of data in an XML document. The user can define the tags for components within the document. The user can also add attributes to these tags as necessary. In addition, the user defines how the components fit together. Therefore, XML is a tool that allows various information, such as text, tables, tracings and graphs, to be transmitted over the worldwide web via an Internet or other connection to a remote location. However, XML, unlike HTML, comes with no formatting conventions and always needs a stylesheet to be displayed.

In accordance with the further aspect of the present invention, the XML formatted Patient Session Information is subjected to transformation by a human language specific stylesheet, e.g., an XSL stylesheet, into XSL transformed Patient Session Information. The XSL stylesheet effects translation of the XML formatted Patient Session Information into HTML or another XML or another suitable format, e.g., PDF or SVG graphic image formats. The XSL transformed Patient Session Information is thereby rendered understandable to the user that selects the human language when the translated Patient Session Information is visually displayed or printed out or rendered audible upon command by the user. The translated Patient Session Information can also be stored in the programmer memory or in the IMD memory or transferred or exported to another device or system interconnected with the programmer.

The XSL stylesheet consists of two parts: (1) a language for transforming XML documents (XSLT), and an XML vocabulary for specifying formatting semantics (XSL-VO). An XSL stylesheet specifies the presentation of a class of XML documents by describing how an instance of the class is transformed into an XML document that uses the formatting vocabulary. XSL is described in the Worldwide web Consortium's "Extensible Stylesheet Language Specification," the current working draft of which may be found at http://www.w3.org/TR/WD-xsl (Apr. 21, 1999). An XSL stylesheet processor accepts a document or data in XML and an XSL stylesheet and produces the presentation of that XML source content as intended by the stylesheet. It is contemplated that most major web browser applications will include XSL stylesheet processors which will enable them to convert the combination of XML and XSL data into a form, such as a viewable HTML web page, as specified by the XSL.

In addition to using XSL to specify the rendering style of XML data, cascaded stylesheets (CSS) can also be used as set forth in the Proposed Recommendation dated Apr. 28, 1999 from the Worldwide web Consortium (see http://www.w3.org/TR/1999/xml-stylesheet-19990428). This specification allows an XML stylesheet to be associated with an XML document by including one or more processing instructions with a target of "xml-stylesheet" in the document's prolog. The Worldwide web Consortium's recommendation regarding cascaded stylesheets may be found at http://www.w3.org/TR/REC-CSS1 (Jan. 11, 1999) which specifies level 1 of the Cascading Style Sheet mechanism (CSS1). CSS1 is a simple stylesheet mechanism that allows authors and readers to attach style (e.g. fonts, colors and spacing) to HTML documents. The CSS1 language is human readable and writeable, and expresses style in common desktop publishing terminology.

It should be noted that XML, XSL, CSS and related Internet protocols and specifications are still being defined and extended, a process that can be expected to enhance the ability of the present invention to selectively and attractively provide information about products to those who desire that information from the most knowledgeable and reliable sources of that information.

In accordance with the present invention, stylesheets would be written for transforming XML formatted Patient Session Information for formatting the display of data (using the CSS stylesheet language), formatting the print format (using the CSS or XSL-FO stylesheet language), transforming to other data formats (using the XSLT stylesheet language), and transforming to other local human languages (using the XSLT stylesheet language). The terms "XSL stylesheet" and "XSL formatted" used herein in relation to the function of transforming XML formatted Patient Session Information into a selected other human language understandable to the user shall be understood to specifically involve the use of the XSLT stylesheet language.

FIG. 1 is a simplified schematic view of an IMD 10 comprising a monitor or IPG coupled with a lead extending into the right ventricle implanted in patient 252 associated with a programmer 200, a computer 256 and a remote computer and associated peripherals 260 in a system 250 of the present invention. The IMD 10 can be employed in the practice of the present invention to acquire or store Patient Session Information including data that is downlink telemetry (DT) transmitted to the IMD 10 by programmer 200. The Patient Session Information can be retrieved in an uplink telemetry (UT) transmission upon receipt of a DT transmitted interrogation command and displayed, printed out, stored in memory or audibly stated in by the external programmer 200.

A user either employs the programmer 200 in a contemporaneous telemetry session with the IMD 10 to retrieve Patient Session Information and to transform it into a human language understandable to the user. Or the user uses the local computer 256 either in a connection with programmer 200 in a contemporaneous telemetry session with the IMD 10 or to access stored Patient Session Information relating to an earlier telemetry session and to transform it into a human language understandable to the user. Or the user uses the local computer 256 to access Patient Session Information stored on a remote database 284 of data center or server 282 through an Internet connection 258/262 and to transform it into a human language understandable to the user that is displayed or printed from the local computer 256. In this case, the local computer 256 may be remote from the patient, e.g., in a physician's office, and not coupled to the programmer 200 in any way except possibly through the Internet connections 258/262.

The XML formatted Patient Session Information and XSL stylesheet files can be provided to a web browser through any commercial web server. A web server is a software package that runs on a networked server e.g., server 282, and provides files over a network e.g., Internet 400.

A stand-alone storage system such as computer 256 could make the data available directly through its own web browser. Web browsers are also capable of viewing locally stored files. In this configuration a web server 282 would not be necessary.

In a one exemplary variation of the present invention, the XML converter and the XSL stylesheet are installed in the programmer 200 so that conversion and translation functions are performed by a user using the programmer 200. In another variation, the XML converter is installed in the IMD 10 and the XSL stylesheet is installed in the programmer 200, so that XML formatted Patient Session Information is UT transmitted from IMD 10 to programmer 200 and transformed into a human language understandable to the user The XSL transformed Patient Session Information can be transferred to a local computer 256 directly or indirectly coupled to the programmer 200 or to a remote computer or data center or server 282 accessible through the Internet 400. The connection between the local computer 256 and the programmer 200 can be made via a hard-wired connection or the manual transfer of a data file, e.g., on a floppy disk 280.

In a further exemplary variation particular to use of an external patient monitor and a local computer 256, the UT transmitted Patient Session Information received by the external patient monitor (taking the place of programmer 200) is transferred to the local computer 256. The XML converter and the XSL stylesheet are installed in the local computer 256 so that the above-described functions are performed using the local computer 256. The transferred Patient Session Information is formatted into XML formatted Patient Session Information in the local computer 256. The connection between the local computer 256 and the external patient monitor can be made via a hard-wired connection or the manual transfer of a data file, e.g., on a floppy disk 280.

However, the data transfers from the programmer 200 or external patient monitor to the local computer 256 or the remote computer or data center or server 282 can be through the Internet 400 if the programmer 200 or external patient monitor has the capability of making the Internet connection 258.

The XML formatted Patient Session Information is formatted either in the programmer 200 or in an external patient monitor that receives UT transmissions from the IMD when the patient is in the vicinity and other conditions are met. Or the Patient Session Information is formatted in the IMD itself so that XML formatted Patient Session Information is uplink telemetry transmitted to the programmer or external patient monitor. The XML formatted Patient Session Information is then transferred in any of the known manner to local computer 256 directly or indirectly coupled to the programmer 200 or external patient monitor or to a remote computer or data center or server 282 through an Intranet or Internet connection or any of the above-listed and any other known data transfer mechanisms.

In these cases, the XML formatted Patient Session Information can be permanently or temporarily stored in memory at the local computer 256 or memory of a remote computer or a database 284 of a data center or server 282. The XML formatted Patient Session Information can be accessed by a user at the time or transfer or later in time and rendered understandable to the user who selects the human language XSL stylesheet of his/her choice.

In networked applications, the XSL stylesheets would reside in server 282 and not need to be distributed to every customer accessing the server 282 through the Internet 400, e.g., via local computer 256. Even customer resident systems can access the XSL stylesheets from the server 282 to transform XML formatted Patient Session Information stored in local memory or being retrieved in real time from the IMD through the programmer 200.

The IMD 10 shown in FIG. 1 can be a bradycardia pacemaker or anti-tachyarrhythmia device comprising at least one of pacing and sensing leads 16 and 18 attached to connector module 12 of hermetically sealed enclosure 14 of the pacemaker IPG and implanted near human or mammalian heart 8. Or, IMD 10 can be a monitor, e.g., the above-mentioned CHRONICLE™ IHM coupled with a sensing lead 16 and a pressure sensor bearing lead 18 attached to connector module 12 of hermetically sealed enclosure 14 and implanted near human or mammalian heart 8 or an implantable monitoring device such as that disclosed in U.S. Pat. No. 5,331,966. Alternatively, IMD 10 may be an implantable nerve stimulator or muscle stimulator. The present invention is believed to find wide application in conjunction with data storage and retrieval in any form of IMD having data storage and telemetry capabilities.

Figure 2:
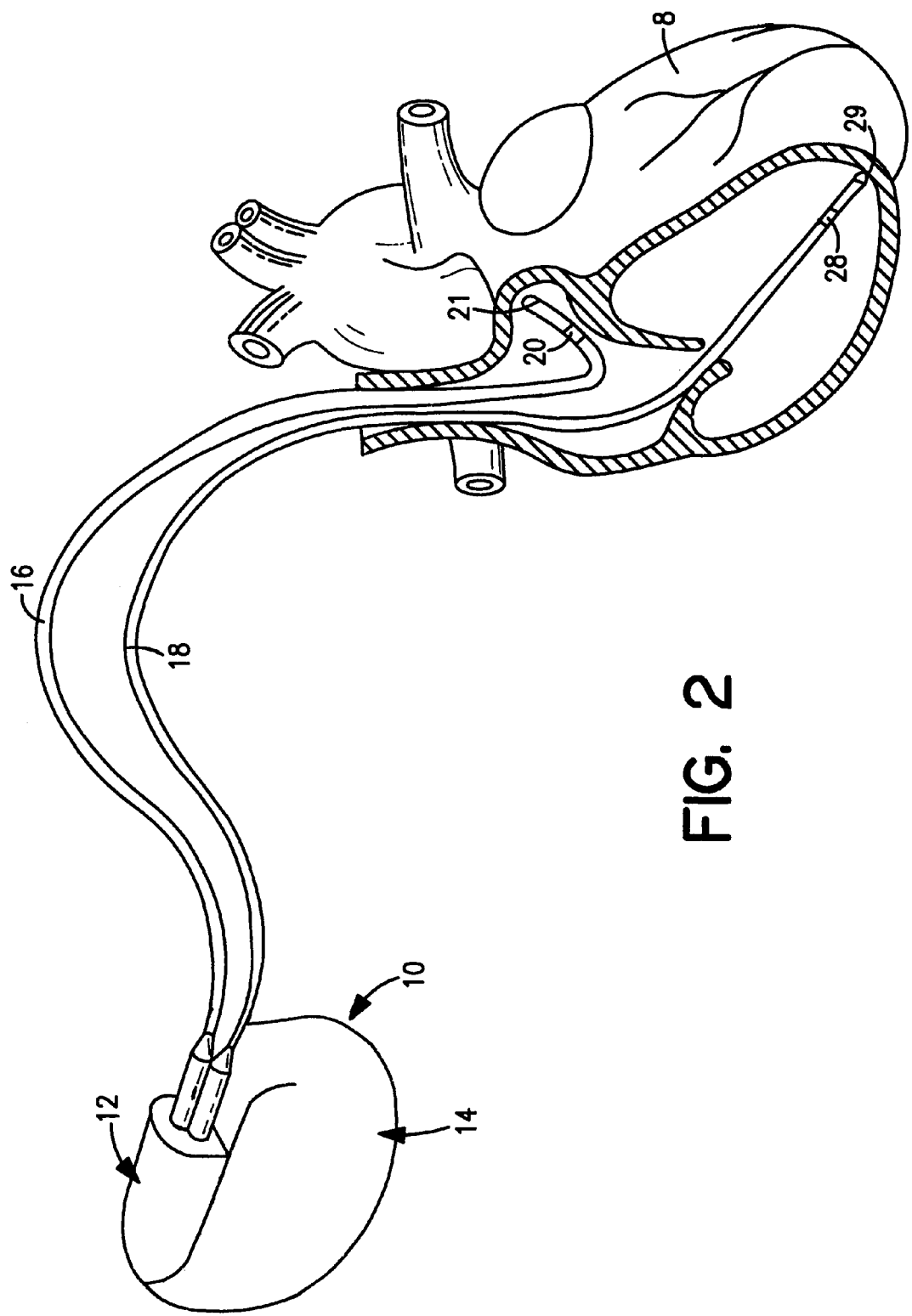
FIG. 2 is a simplified illustration of a dual chamber pacemaker IPG coupled with leads extending into the right atrium and right ventricle and locating pace/sense electrodes therein.

FIG. 2 is a simplified illustration of a dual chamber pacemaker IPG coupled with leads 16 and 18 extending into the right atrium and right ventricle and locating pace/sense electrodes therein. Atrial electrodes 20 and 21 disposed at the distal end of atrial pacing lead 16 are located in the right atrium to sense the atrial EGM and P-waves attendant to the depolarization and re-polarization of the atrium. Ventricular electrodes 28 and 29 disposed at the distal end of ventricular pacing lead 18 are located in the right ventricle to sense the ventricular EGM and R-waves attendant to the depolarization and re-polarization of the right ventricle. Pacing and sensing leads 16 and 18 further provide pacing pulses for causing depolarization of cardiac tissue in the vicinity of the distal ends thereof. Leads 16 and 18 may have unipolar or bipolar electrodes disposed thereon, as is well known in the art.

Figure 3:
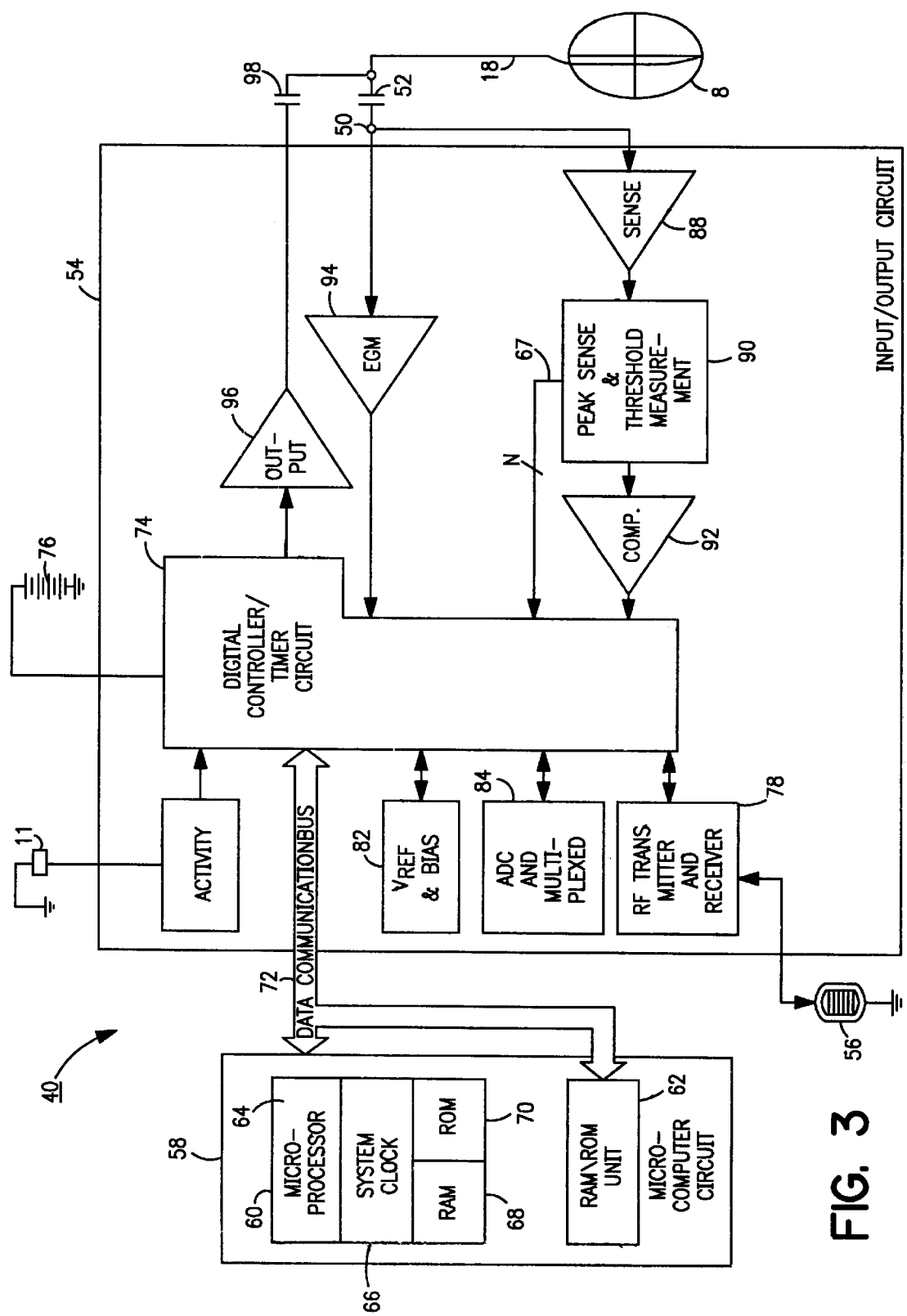
FIG. 3 is a block diagram illustrating the constituent components of a pacemaker of the type depicted in FIGS. 1 and 2.

FIG. 3 shows a block diagram illustrating the constituent components of IMD 10 in accordance with one embodiment of the present invention, where IMD 10 comprises a pacemaker IPG 40 having a microprocessor-based architecture. Electrical components shown in FIG. 3 are powered by an appropriate implantable battery power source 76 in accordance with common practice in the art. For the sake of clarity, the coupling of battery power to the various components of IPG 40 is not shown in the figures.

As shown in FIG. 3, lead 18 is coupled to node 50 in IPG 40 through input capacitor 52. For the sake of convenience, IPG 40 in FIG. 3 is shown with lead 18 only connected thereto. However, it is understood that similar circuitry and connections not explicitly shown in FIG. 3 apply to lead 16 (shown in FIGS. 1 and 2).

Microcomputer circuit 58 preferably comprises on-board circuit 60 and off-board circuit 62. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

IPG 40 is shown as including activity sensor 11 that typically (although not necessarily) provides a sensor output that varies as a function of a measured parameter relating to a patient's metabolic requirements. Activity sensor 11 is most preferably attached to a hybrid circuit located inside hermetically sealed enclosure 14 of IPG 40. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The pacing rate is controlled by software-implemented algorithms stored within microcomputer circuit 58 and is preferably adjusted to the activity level of the patient in a manner well know in the art.

Figure 6:
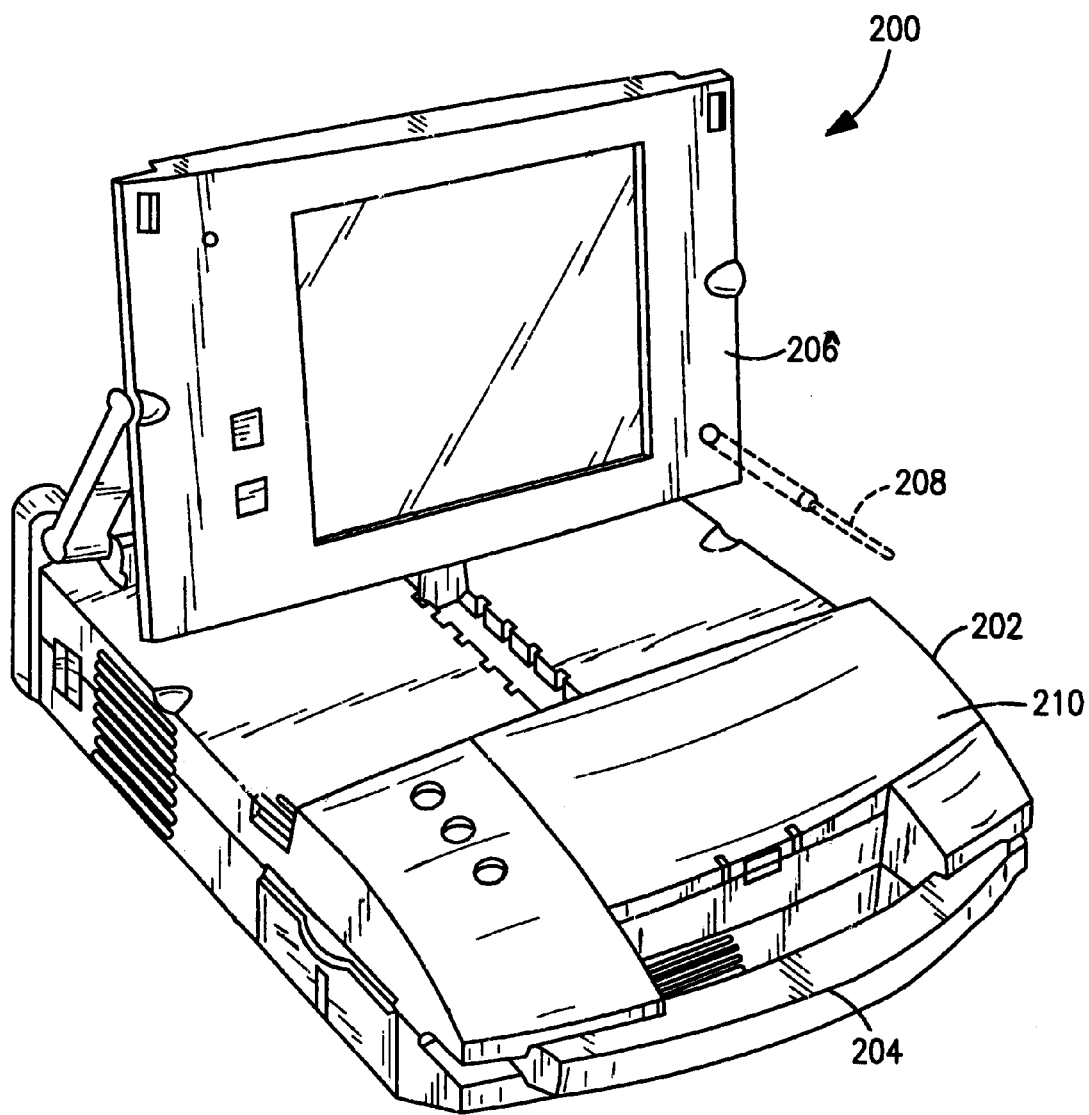
FIG. 6 is a perspective view of a programmer used in conjunction with an IMD of FIGS. 1–5, for example, to program operating modes and parameter values, to store patient data in IMD memory and to retrieve such data in a telemetry session.

IPG 40 in FIG. 3 is most preferably programmable by means of an external programming unit (shown in FIG. 6). One such programmer is the commercially available Medtronic Model 9790 programmer, which is microprocessor-based and provides a series of encoded signals to IPG 40, typically through a programming head that transmits or telemeters radio-frequency (RF) encoded signals to IPG 40. Any of a number of suitable programming and telemetry methodologies known in the art may be employed so long as the desired information is DT transmitted to and UT transmitted from the IPG 40.

Antenna 56 is connected to input/output circuit 54 to permit uplink/downlink telemetry through RF transmitter and receiver telemetry unit 78. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92.

The electrogram signal provided by EGM amplifier 94 is employed when IPG 40 is being interrogated by an external programmer to transmit a representation of a cardiac analog EGM in an uplink telemetry transmission to the external programmer. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" uplink telemetry transmission of EGM signals and battery end-of-life (EOL) replacement functions. Operating commands for controlling the timing of IPG 40 are coupled from microprocessor 64 via data bus 72 to digital controller/timer circuit 74, where digital timers and counters establish the overall escape interval of the IPG 40 as well as various refractory, blanking and other timing windows for controlling the operation of peripheral components disposed within input/output circuit 54.

The IPG 40 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IPG 40 may be programmably configured to operate so that it varies the rate at which it delivers stimulating pulses to heart 8 in response to one or more selected sensor outputs being generated. Numerous pacemaker features and functions not explicitly mentioned herein may be incorporated into IPG 40 while remaining within the scope of the present invention.

The present invention is not limited in scope to single-sensor or dual-sensor pacemakers or to the use of activity or pressure sensors. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers of the type described in U.S. Pat. No. 5,800,465, for example.

Figure 4:
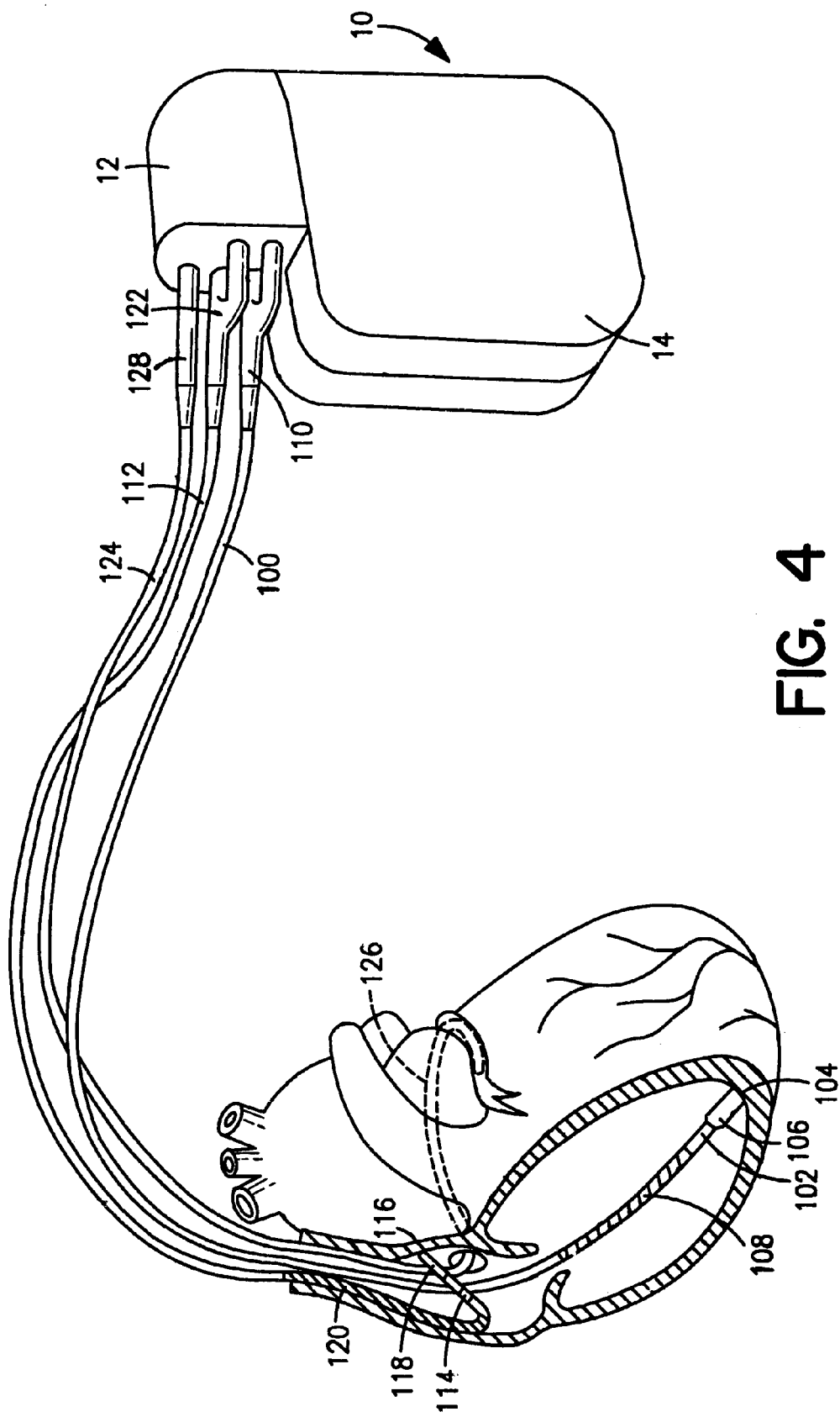
FIG. 4 is a simplified schematic view of an ICD IPG coupled with leads extending into the right atrium, the right ventricle and the coronary sinus and locating cardioversion/defibrillation and pace/sense electrodes therein.
Figure 5:
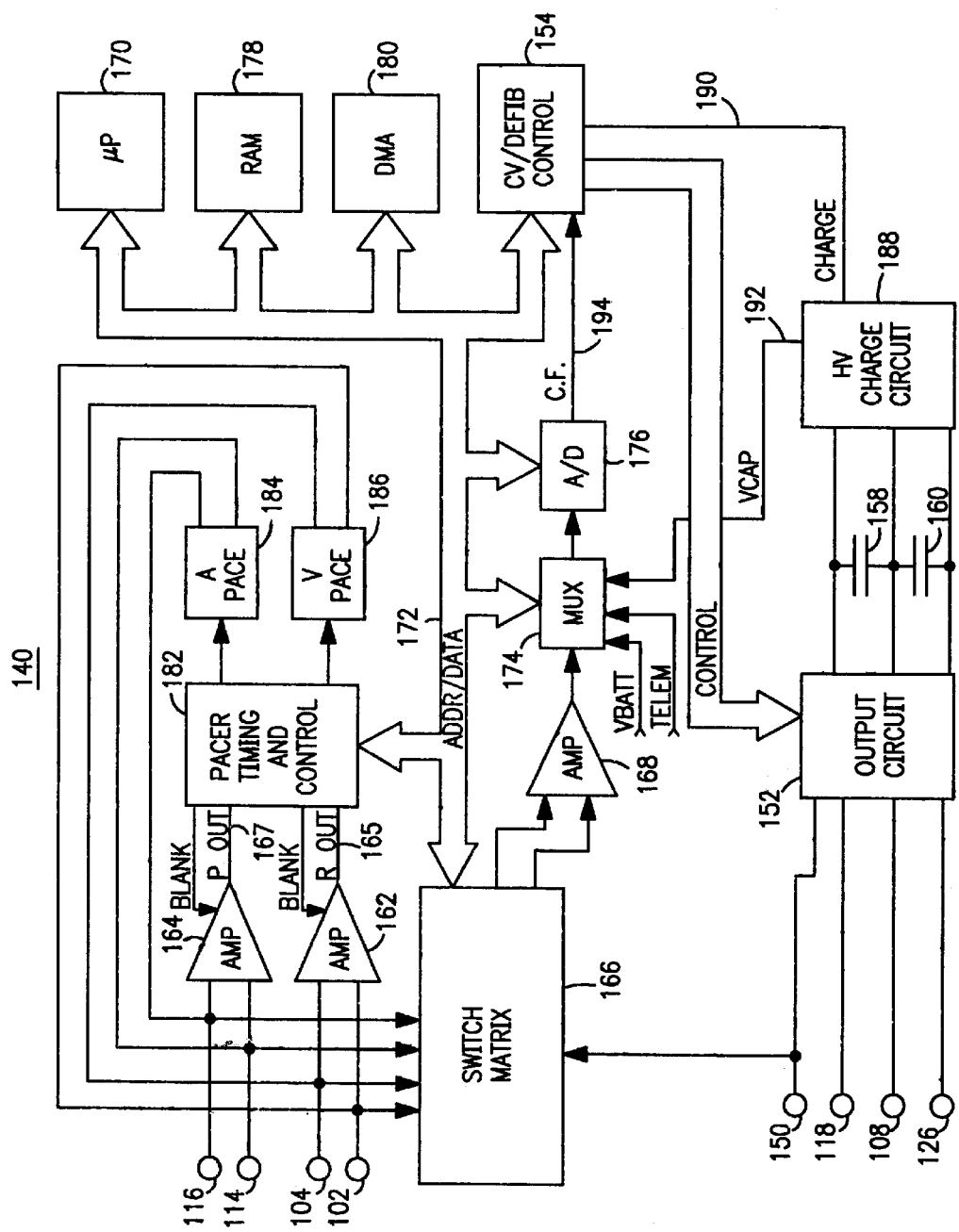
FIG. 5 is a partial block diagram illustrating one embodiment of an ICD IPG used in conjunction with the present invention.

Thus, IMD 10 may alternatively be an ICD having single or dual chamber pacing and atrial or ventricular cardioversion/defibrillation capabilities corresponding to any of numerous commercially available ICDs. FIGS. 4 and 5 illustrate one embodiment of IMD 10 and a corresponding lead set of the present invention, where IMD 10 is an ICD comprising an ICD IPG 140 as shown in FIG. 5 coupled with ventricular lead 100, atrial lead 112 and coronary sinus (CS) lead 124.

In FIG. 4, the ventricular lead 100 includes an elongated insulative lead body carrying three concentric coiled wire conductors separated from one another by tubular insulative sheaths. Ring electrode 102, extendable helix electrode 104 mounted retractably within insulative electrode head 106 and elongated cardioversion/defibrillation coil electrode 108 are located in the distal portion of lead 100 and positioned within the right ventricle. Elongated coil electrode 108 may be fabricated from platinum, platinum alloy or other materials known to be usable for delivering cardioversion/defibrillation shocks and may be about 5 cm in length. Electrodes 102 and 104 are employed for cardiac pacing and for sensing the ventricular EGM and R-waves accompanying ventricular depolarizations. Each of the electrodes 102, 104 and 108 is coupled to one of the coiled conductors within the lead body of ventricular lead 100. Bifurcated connector 110 at the proximal end of the ventricular lead 100 comprises three electrical connectors, each coupled to one of the three coiled conductors, and is inserted into connector receptacles in the connector block 12 of IMD 10.

The atrial lead 112 shown in FIG. 4 can take the form of an elongated insulative lead body enclosing three concentric coiled conductors separated from one another by tubular insulative sheaths corresponding to the structure of the ventricular lead. Ring electrode 114 and extendable helix electrode 116 mounted retractably within an insulative electrode head 118 are located adjacent the J-shaped distal end of the lead body within the right atrium and are each coupled to one of the coiled conductors within lead body of atrial lead 112. Electrodes 114 and 116 are employed for atrial pacing and for sensing the atrial EGM and P-wave accompanying atrial depolarizations. Elongated cardioversion/defibrillation coil electrode 120 is provided proximal to electrode 114 and coupled to the third conductor within lead body. Electrode 120 preferably is 10 cm in length or greater and is configured to extend from the SVC toward the tricuspid valve. In one embodiment of the present invention, approximately 5 cm of the coil electrode 120 is located in the right atrium with the remaining 5 cm located in the SVC. Bifurcated connector 122 has three electrical connectors each coupled to one of the coiled conductors is located at the proximal end of the atrial lead 124 and is inserted into connector receptacles in the connector block 12 of IMD 10.

The CS lead 124 shown in FIG. 4 can take the form of a CS lead disclosed in the above cited '838 patent and includes elongated insulative lead body enclosing one coiled wire conductor coupled to an exposed elongated cardioversion/defibrillation coil electrode 126 (illustrated in broken outline in FIG. 4). Elongated cardioversion/defibrillation coil electrode 126 may be about 5 cm in length and is located within the CS and great vein of the heart adjacent to the left ventricle. A connector plug 128 carrying an electrical connector coupled to the coiled conductor is located at the proximal end of the lead and is inserted into a connector receptacle in the connector block 12 of IMD 10.

Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention.

FIG. 5 is a functional schematic diagram of one embodiment of ICD IPG 140 that can be employed in the practice of the present invention. ICD IPG 140 is coupled with pace/sense electrodes 102, 104 and 114, 116 shown in FIG. 4 and with cardioversion/defibrillation electrodes 105, 118 and 126 shown in FIG. 4 as well as a further electrode 150 comprising the uninsulated portion of the housing 14. Electrodes 108, 118, 126 and 150 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of a capacitor bank (which includes capacitors 158 and 160) during delivery of defibrillation shocks.

Electrodes 102 and 104 are located on or in the ventricle of the patient and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium of the patient and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold.

Switch matrix 166 is used to select which of the available electrodes are coupled to wide band (0.5–200 Hz) amplifier 168 for use in digital signal analysis. Selection of electrodes is controlled by microprocessor 170 via data/address bus 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 102, 104, 112 and 116. Escape interval counters are also reset on generation of pacing pulses and thereby control the basic timing of cardiac pacing functions, including anti-tachyarrhythmia pacing. The durations of the intervals defined by escape interval timers are determined by microprocessor 170 via data/address bus 172. The value of the count present in the escape interval counters when reset by sensed R-waves and P-waves may be used to measure the durations of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 182 corresponding to the occurrence of sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182 via data bus 172, to control the operation of the escape interval counters therein and to define refractory periods during which detection of R-waves and P-waves is ineffective to restart the escape interval counters.

In the event that generation of a cardioversion or defibrillation shock is required, microprocessor 170 may employ an escape interval counter to control timing of such cardioversion and defibrillation shocks, as well as associated refractory periods. Microprocessor 170 activates cardioversion/defibrillation control circuitry 154, which initiates charging of high voltage capacitors 158 and 160 via charging circuit 188, under the control of high voltage charging control line 190 in response to the detection of atrial or ventricular fibrillation or tachyarrhythmia requiring a cardioversion/defibrillation shock. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion shock is controlled by pacer timing/control circuitry 182. Following delivery of the fibrillation or tachycardia therapy microprocessor 170 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation shocks and for controlling the timing functions related to them are disclosed in U.S. Pat. No. 5,188,105, for example. Any known cardioversion or defibrillation shock control circuitry is believed to be usable in conjunction with various embodiments of the present invention, however.

Continuing to refer to FIG. 5, delivery of cardioversion or defibrillation shocks is accomplished by output circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators.

FIG. 6 is a perspective view of programmer 200 used in conjunction with the present invention. Programmer unit 200 has various features, including outer housing 202, carrying handle 204, articulate display screen 206, stylus 208, and analyzer 210. Programmer 200 may take the form of that disclosed in the above-referenced Model 9790 Programmer or the programmer described in the above-referenced '076 patent.

Display screen 206 is disposed on the upper surface of housing 202. Display screen 206 folds down in a closed position when programmer 200 is not in use, thereby reducing the size of programmer 200 and protecting the display surface of display screen 206 during transportation and storage. In the perspective view of FIG. 6, programmer 200 is shown with articulate display screen 206 having been lifted up into one of a plurality of possible open positions such that the display area is visible to a user situated in front of programmer 200. Display screen 206 is preferably an LCD or electroluminescent type, characterized by being relatively thin as compared to a cathode ray tube display, or the like. Display screen 206 is operatively coupled to computer circuitry disposed within housing 202 and is adapted to provide a visual display of graphics and/or alphanumeric data under control of the computer circuitry.

Display screen 206 is provided with touch-sensitivity capability, such that a user can interact with the internal computer by touching the display area of display screen 206 with stylus 208. It is believed that those of ordinary skill in the computer will be familiar with touch-sensitivity display technology, and the details of implementation of such display will not be described further herein. Display screen 206 is the primary input medium for programmer 200, and therefore preferably has sufficient resolution to support operations including selection, annotation, and character recognition.

Analyzer 210, which in prior art devices was a separate unit capable of connection to programmer 200 only via connecting cables, provides a medium for an operator to run a series of diagnostic tests during an implantation procedure of an IMD, such as IMD 10 previously discussed. For example, a continuous-time waveform or a single complex waveform can be analyzed by analyzer 210 and displayed on display screen 206 from a variety of implanted leads, such as a lead positioned in an atrium or ventricle of heart 8 (shown in FIGS. 1, 2 and 4).

Figure 7:
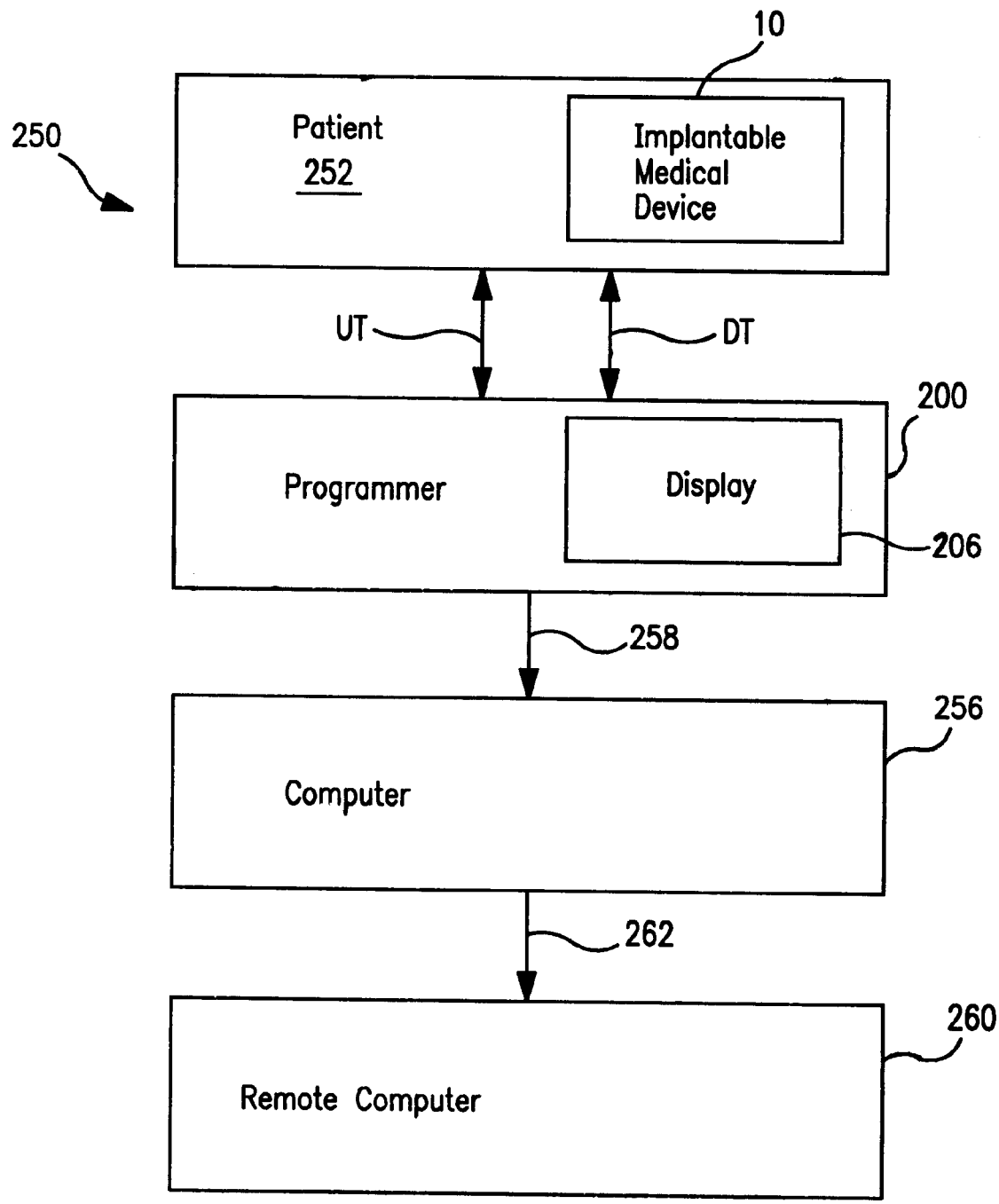
FIG. 7 illustrates the data flow between the IMD, the programmer, a local computer and a remote computer or server of FIG. 1.

FIG. 7 is a block diagram showing system 250 of FIG. 1, which includes IMD 10 within patient 252, uplink and downlink telemetry transmissions UT and DT during a telemetry session, programmer 200 having display 206, computer 256, connection 258, remote computer 260, and connection 262. System 250 can be used at any time when it is necessary or desirous to store information relating to IMD 10 or generate a report based on information received from IMD 10, including previously stored patient data, in computer 258 and/or remote computer 260 at a remote location.

As shown in FIGS. 1 and 7, programmer 200 is interconnected in a telemetry session with IMD 10 providing radio-frequency communications via alternating UT and DT transmissions between programmer 206 and IMD 10. A technician or other medical support staff can establish a communication link in a telemetry session and retrieve various information stored within IMD 10 in an UT transmission from IMD 10 to programmer 200. Connection 258 interconnects programmer 200 with computer 256 either in a hard-wired LAN connection or an Internet connection as shown in FIG. 1, if the programmer 200 can directly communicate through the Internet 400. Connection 258 can therefore be any type of connection that facilitates the transfer of information between programmer 200 and computer 256, particularly patient data received in an UT transmission. Typically, a programmer 200 available at the present time does not include a modem or any other capability of directly interconnecting with the Internet 400. And so, the typical connection 258 would be a hard-wired connection with computer 256 located at the same site with the IMD 10 and the programmer 200. Or, as shown in FIG. 1, a data transfer can be effected through storage of the UT transmitted patient data received by programmer 200 on a storage medium 280, e.g., a floppy disk, that is then manually inserted into a disk drive of computer 256 so that it can be then made available through connection 262 to remote computer 260.

Remote computer 260 is positioned at a location more remote from computer 256, programmer 200, and patient 252 and can either be connected to the local computer 256 or the programmer 200 if it is capable of communication over the Internet 400. The remote computer 282 is depicted in association with peripherals, including modem 286, telephone 288 and printer/scanner/facsimile machine 290. It will be assumed that local 256 would also be coupled with a modem, telephone, and one or more of a printer, scanner and facsimile machine.

Thus, connections 258 and 262 can be any type of connection that interconnects computer 256 with remote computer 260, e.g. a local area network (LAN) connection, if the remote computer 260 is located in the same facility. As shown in FIG. 1, the connection 258/262 can be an Internet connection effected through a DSL modem 286 and a telephone line connection from the telephone 288 for example.

Figure 8:
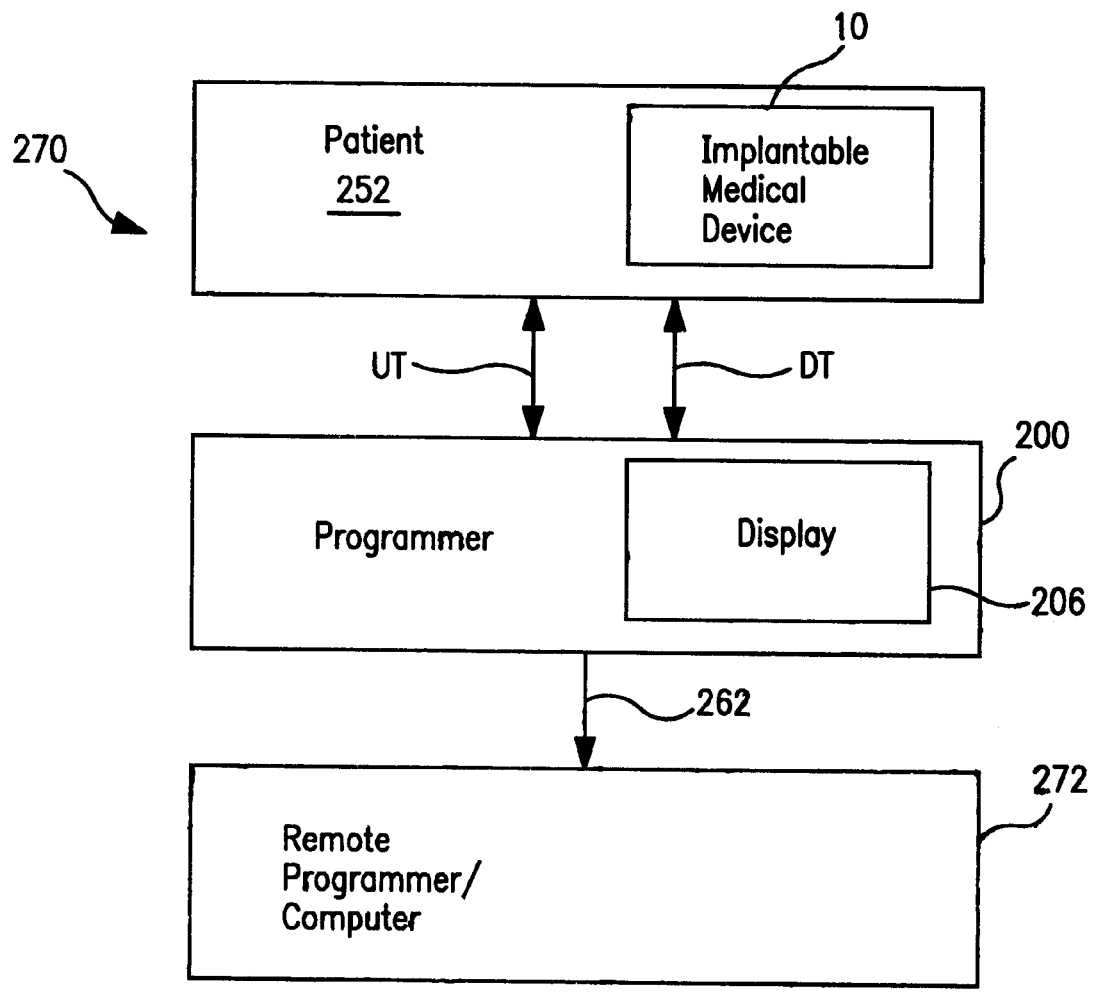
FIG. 8 illustrates the data flow between the IMD, the programmer, a local computer and a remote programmer and computer of FIG. 1.

System 270, shown in FIG. 8, is similar to system 250 shown in FIG. 7. However, computer 272 of FIG. 7 has been removed and remote computer 276 of FIG. 7 has been replaced by remote programmer/computer 272. Remote programmer/computer is interconnected to programmer 200 via connection 262, which is identical to connection 262 of FIG. 7. With today's technology, programmers, such as programmer 200, include a microprocessor and has the basic capabilities of a personal computer. Thus, programmer 200 can create a computer file of digitized patient data received in an UT transmission from IMD 10 and send the computer file to remote programmer/computer 272 via connection 262. Once again, connection 262 could be LAN connection, a telephone line connection, an Internet connection or a radio frequency connection.

The data stored within IMD 10 can relate to a wide range of information in conjunction with IMD 10 and/or the patient 252. For example, specific demographics of patient 252 can be stored within IMD 10, such as the gender, age, and past medical history and other patient data of the type described in the above-referenced '076 patent. The IMD data stored within IMD 10 includes the identification of the IMD itself, including identification of both the IPG and the associated leads, information relating to current programmed operating modes and parameters and a historic record of previously programmed operating modes and states, accumulated data relating to therapies delivered, detection of trigger events triggering delivery of therapies, success or failure of delivered therapies and the like, battery status, lead impedance data and many other forms of IMD data as are well known in the art.

All of the data stored within IMD 10 including the Patient Session Data can be UT transmitted to programmer 200 in a memory dump procedure wherein the patient data and IMD data from IMD 10 is UT transmitted to programmer 200 without changing the format of the data. As noted above, most IMDs utilize various formats, such as waveform encoding formats, numeric formats, binary formats, and the ASCII format for data storage in IMD memory.

When the selected information is transferred from either programmer 200 or computer 256 to remote access computer 316 (shown as remote computer 260 in FIG. 7 and as remote programmer/computer 272 in FIG. 8), it can be sent via an Internet connection such as a local area network (LAN), a telephone line connection, or a radio frequency connection. In addition, remote access computer 316 can be a computer operating on the same system as programmer 200 or computer 256 (shown in FIG. 7) or operation on a distinct system. The use of XML format permits this flexibility.

Figure 9:
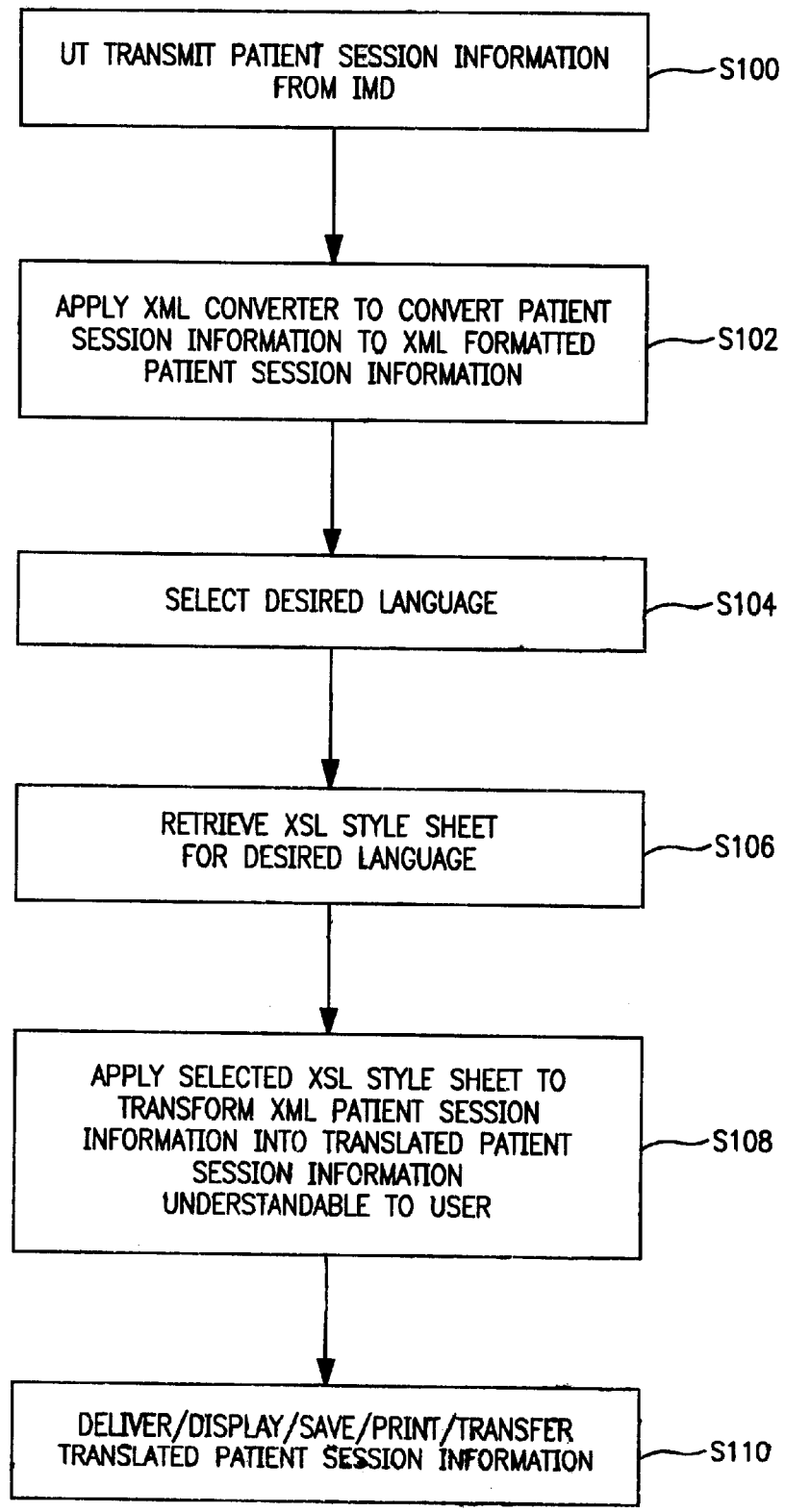
FIG. 9 illustrates the transformation of Patient Session Information into XML formatted Patient Session Information and XSL transformed Patient Session Information translated into a human language understandable by a user in accordance with the various embodiments of the invention.

FIG. 9 illustrates the transformation of Patient Session Information into XML formatted Patient Session Information and XSL transformed Patient Session Information in accordance with the various embodiments of the invention.

In steps S100 and S102, the Patient Session Information is provided in the XML format in a number of ways described above. For example, step S100 is performed in a UT transmission between the IMD and either a programmer or a local or remote computer or an external patient monitor. The XML converter applied in step S102 can be located in the IMD or in any of the programmer or local or remote computer or the external patient monitor. Thus, XML formatted Patient Session Information is created and then stored temporarily until the remaining steps S104–S110 are completed or for a longer term in memory of a local computer, a programmer/computer or a database of a remote data center or server accessible through the Internet.

The selection of the desired language understandable by the user depends upon where the XML formatted Patient Session Information is being stored and what access device is being used by the user to access it.

During a telemetry session employing a programmer, the user can select the language from a menu displayed on the programmer display. The language of the XML formatted Patient Session Information can be observed or automatically detected. If the XSL style sheet that effects translation from the language of the XML formatted Patient Session Information is resident in the programmer memory or a CD-ROM or other memory device, it can be automatically or manually selected in step S104 to perform steps S106 and S108.

During a telemetry session employing a local computer coupled with the programmer, the user can also select the language from a menu. The language of the XML formatted Patient Session Information can be observed or automatically detected, and the language of the operating system of the computer coupled with the programmer receiving the XML formatted Patient Session Information from the IMD can be automatically detected. If the XSL style sheet that effects translation from the language of the XML formatted Patient Session Information is resident in the computer memory or a CD-ROM or other memory device, it can be automatically or manually selected in step S104 to perform steps S106 and S108. If the computer is coupled with the Internet, the web site where the XSL style sheet is resident can be accessed and the XSS style sheet can be downloaded to be employed in steps S106 and S108.

Step S104 can be performed in a similar manner if the user is employing the local computer to access the XML formatted Patient Session Information stored in the database of a remote data center of server. The language selection of the user's web browser could be detected, and steps S106 and S108 could be automatically performed by the server or remote data center upon the accessed XML formatted Patient Session Information. Or, the user may be requested to identify the language. In this way, the XSL style sheet can be applied at the remote data center or server to transform the accessed XML formatted Patient Session Information into translated Patient Session Information delivered in step S110.

Thus, the indication by the user of a desired language that the accessed XML formatted Patient Session Information be delivered, displayed, saved, printed or transferred in per step S110 causing the selection of step S104 to take place can be automatic or manually made by the user.

In step S106, the human language specific XSL stylesheet for transforming the first human language of the XML formatted patient session information into the human language understandable and selected by the user in step S104 is retrieved. The human language specific XSL stylesheet is applied to transform the XML formatted patient session information into translated patient session information in the human language understandable by the user in step S108. Step S108 can be performed either in the programmer operated by the user, a local computer coupled to the programmer operated by the user, the local computer operated by the user to access a database of a server or data center or the server or data center itself. Thus, the human language XSL stylesheets can be distributed and installed for selection, retrieval and application in a variety of places that are most efficient and efficacious depending upon how the XML formatted Patient Session Information is accessed, stored and distributed.

The writing of stylesheets, e.g., XSL stylesheets, for all desired human languages is much easier than writing language translation software, and therefore can be completed faster at much less cost. The XSL stylesheets can be easily installed on a web server and can be accessed through a web browser for use at the site or downloading to a user's personal computer and installation in the programmer. In HTML displays, the user is presented with a display of the XSL stylesheet button that can be selected to apply the language translation. Or, the XSL stylesheet can be automatically retrieved and applied by detecting the human language set for computer operating system or web browser.

Once XML formatted Patient Session Information is translated in step S108, it is delivered to the user's computer, if step S106 is performed remotely, and it is displayed and/or saved and/or printed and/or transferred in step S110.

All patents and publications referenced herein are incorporated herein by reference in their entireties.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. In relation to an implantable medical device (IMD), a method of providing patient session information including patient data and IMD data stored in IMD memory in a human language understandable to a user comprising the steps of:

providing extensible mark-up language (XML) formatted patient session information in a first human language;

in response to an indication by the user, providing a human language specific stylesheet for transforming the first human language of the XML formatted patient session information into the human language understandable by the user;

applying the human language specific stylesheet to transform the XML formatted patient session information into translated patient session information in the human language understandable by the user; and providing the translated patient session information to the user.

2. The method of claim 1, wherein the stylesheet comprises a human language specific extensible stylesheet language (XSL) stylesheet.

3. The method of claim 1, wherein the applying step further comprises translating the XML formatted patient session information into the understandable human language in a format selected from the group comprising an HTML format, another XML format, a PDF graphic image format or an SVG graphic image format.

4. The method of claim 1, wherein the step of providing the translated patient session information to the user comprises visually displaying the translated patient session information on a visual display or printout.

5. The method of claim 1, wherein the step of providing the XML formatted patient session information in a first human language further comprises the steps of:

transferring the XML formatted patient session information to a remote data center and storing the XML formatted patient session information in a remote data center database accessible by the user; and accessing the XML formatted patient session information in a remote data center database.

6. The method of claim 1, wherein the step of providing the XML formatted patient session information in a first human language further comprises the steps of:

transferring the XML formatted patient session information over the Internet to a remote server and storing the XML formatted patient session information in a remote server database accessible by the user employing a web browser;

initiating an Internet connection between a user controlled Internet access device operating a web browser; and accessing the XML formatted patient session information in the remote server database through the web browser.

7. The method of claim 1, wherein the step of providing the XML formatted patient session information in a first human language further comprises:
   storing the patient session information in a first format in IMD memory;
   initiating a telemetry session between an external medical device and the IMD storing patient session information in the first format;
   uplink telemetry transmitting the patient session information stored in the IMD in the first format to the external medical device; and
   converting the uplink telemetry transmitted patient session information from the initial format to the XML format within the external medical device.

8. The method of claim 7, wherein the external medical device is an IMD programmer.

9. The method of claim 7, wherein the external medical device is an external patient monitor.

10. The method of claim 7, wherein the step of providing the XML formatted patient session information in a first human language further comprises the steps of:
    transferring the XML formatted patient session information to a remote data center and storing the XML formatted patient session information in a remote data center database accessible by the user; and
    accessing the XML formatted patient session information in the remote data center database.

11. The method of claim 7, wherein the step of providing the XML formatted patient session information in a first human language further comprising the steps of:
    transferring the XML formatted patient session information over the Internet to a remote server and storing the XML formatted patient session information in a remote server database accessible by the user employing a web browser;
    initiating an Internet connection between a user controlled Internet access device operating a web browser; and
    accessing the XML formatted patient session information in the remote server database through the web browser.

12. The method of claim 1, wherein the step of providing the XML formatted patient session information in a first human language further comprises:
    storing the patient session information in a the XML format in IMD memory;
    initiating a telemetry session between an external medical device and the IMD storing patient session information in the XML format; and
    uplink telemetry transmitting the patient session information stored in the IMD in the XML format to the external medical device.

13. The method of claim 12, wherein the external medical device is an IMD programmer.

14. The method of claim 12, wherein the external medical device is an external patient monitor.

15. The method of claim 12, wherein the step of providing the XML formatted patient session information in a first human language further comprises the steps of:
    transferring the XML formatted patient session information to a remote data center and storing the XML formatted patient session information in a remote data center database accessible by the user; and
    accessing the XML formatted patient session information in the remote data center database.

16. The method of claim 12, wherein the step of providing the XML formatted patient session information in a first human language further comprises the steps of:
    transferring the XML formatted patient session information over the Internet to a remote server and storing the XML formatted patient session information in a remote server database accessible by the user employing a web browser;
    initiating an Internet connection between a user controlled Internet access device operating a web browser; and
    accessing the XML formatted patient session information in the remote server database through the web browser.

17. In relation to an implantable medical device (IMD), a system providing patient session information including patient data and IMD data stored in IMD memory in a human language understandable to a user comprising:
    means for providing extensible mark-up language (XML) formatted patient session information in a first human language;
    means operable in response to an indication by the user for providing a human language specific stylesheet for transforming the first human language of the XML formatted patient session information into the human language understandable by the user;
    means for applying the human language specific stylesheet to transform the XML formatted patient session information into translated patient session information in the human language understandable by the user; and
    means for providing the translated patient session information to the user in the language understandable by the user.

18. The system of claim 17, wherein the stylesheet comprises a human language specific extensible stylesheet language (XSL) stylesheet.

19. The system of claim 17, wherein the applying means further comprises means for translating the XML formatted patient session information into the understandable human language in a format selected from the group comprising an HTML format, another XML format, a PDF graphic image format or an SVG graphic image format.

20. The system of claim 17, wherein the means for providing the translated patient session information to the user comprises means for visually displaying the translated patient session information on a visual display or printout.

21. The system of claim 17, wherein the means for providing the XML formatted patient session information in a first human language further comprises:
    means for transferring the XML formatted patient session information to a remote data center and storing the XML formatted patient session information in a remote data center database accessible by the user; and
    means for accessing the XML formatted patient session information in a remote data center database.

22. The system of claim 17, wherein the means for providing the XML formatted patient session information in a first human language further comprises:
    means for transferring the XML formatted patient session information over the Internet to a remote server and storing the XML formatted patient session information in a remote server database accessible by the user employing a web browser;
    means for initiating an Internet connection between a user controlled Internet access device operating a web browser; and
    means for accessing the XML formatted patient session information in the remote server database through the web browser.

23. The system of claim 17, wherein the means for providing the XML formatted patient session information in a first human language further comprises:
- means for storing the patient session information in a first format in IMD memory;
- means for initiating a telemetry session between an external medical device and the IMD storing patient session information in the first format;
- means for uplink telemetry transmitting the patient session information stored in the IMD in the first format to the external medical device; and
- means for converting the uplink telemetry transmitted patient session information from the initial format to the XML format within the external medical device.

24. The system of claim 23, wherein the external medical device is an IMD programmer.

25. The system of claim 23, wherein the external medical device is an external patient monitor.

26. The system of claim 23, wherein the means for providing the XML formatted patient session information in a first human language further comprises:
- means for transferring the XML formatted patient session information to a remote data center and storing the XML formatted patient session information in a remote data center database accessible by the user; and
- means for accessing the XML formatted patient session information in the remote data center database.

27. The system of claim 23, wherein the means for providing the XML formatted patient session information in a first human language further comprises:
- means for transferring the XML formatted patient session information over the Internet to a remote server and storing the XML formatted patient session information in a remote server database accessible by the user employing a web browser;
- means for initiating an Internet connection between a user controlled Internet access device operating a web browser; and
- means for accessing the XML formatted patient session information in the remote server database through the web browser.

28. The system of claim 17, wherein the means for providing the XML formatted patient session information in a first human language further comprises:
- means for storing the patient session information in the XML format in IMD memory;
- means for initiating a telemetry session between an external medical device and the IMD storing patient session information in the XML format; and
- means for uplink telemetry transmitting the patient session information stored in the IMD in the XML format to the external medical device.

29. The system of claim 28, wherein the external medical device is an IMD programmer.

30. The system of claim 28, wherein the external medical device is an external patient monitor.

31. The system of claim 28, wherein the means for providing the XML formatted patient session information in a first human language further comprises:
- means for transferring the XML formatted patient session information to a remote data center and storing the XML formatted patient session information in a remote data center database accessible by the user; and
- means for accessing the XML formatted patient session information in the remote data center database.

32. The system of claim 28, wherein the means for providing the XML formatted patient session information in a first human language further comprises:
- means for transferring the XML formatted patient session information over the Internet to a remote server and storing the XML formatted patient session information in a remote server database accessible by the user employing a web browser;
- means for initiating an Internet connection between a user controlled Internet access device operating a web browser; and
- means for accessing the XML formatted patient session information in the remote server database through the web browser.

33. In relation to an implantable medical device (IMD), a system providing patient session information including patient data and IMD data stored in IMD memory in a human language understandable to a user comprising:
- an external medical device capable of receiving and saving formatted patient session information transmitted to the external medical device from the IMD within external medical device memory and capable of transferring the patient session information to a remote location;
- an extensible mark-up language (XML) converter for converting patient session information from an initial format into XML formatted patient session information;
- a human language specific stylesheet for transforming the first human language of the XML formatted patient session information into the human language understandable by the user;
- means for applying the human language specific stylesheet to transform the XML formatted patient session information into translated patient session information in the human language understandable by the user; and
- means for providing the translated patient session information to the user in the language understandable by the user.

34. The system of claim 33, wherein the stylesheet comprises a human language specific extensible stylesheet language (XSL) stylesheet.

35. The system of claim 33, wherein the applying means further comprises means for translating the XML formatted patient session information into the understandable human language in a format selected from the group comprising an HTML format, another XML format, a PDF graphic image format or an SVG graphic image format.

36. The system of claim 33, wherein the means for providing the translated patient session information to the user comprises means for visually displaying the translated patient session information on a visual display or printout.

37. The system of claim 33, further comprising:
- means for transferring the XML formatted patient session information to a remote data center and storing the XML formatted patient session information in a remote data center database accessible by the user; and
- means for accessing the XML formatted patient session information in a remote data center database.

38. The system of claim 33, further comprising:
- means for transferring the XML formatted patient session information over the Internet to a remote server and storing the XML formatted patient session information in a remote server database accessible by the user employing a web browser;

means for initiating an Internet connection between a user controlled Internet access device operating a web browser; and means for accessing the XML formatted patient session information in the remote server database through the web browser.

39. The system of claim 33, wherein the patient session information is stored in a first format in IMD memory, and the external medical device further comprises:

means for initiating a telemetry session between the external medical device and the IMD storing patient session information in the first format;

means for uplink telemetry transmitting the patient session information stored in the IMD in the first format to the external medical device; and means for converting the uplink telemetry transmitted patient session information from the initial format to the XML format within the external medical device employing the XML converter.

40. The system of claim 39, wherein the external medical device is an IMD programmer.

41. The system of claim 39, wherein the external medical device is an external patient monitor.

42. The system of claim 39, further comprising:

means for transferring the XML formatted patient session information to a remote data center and storing the XML formatted patient session information in a remote data center database accessible by the user; and means for accessing the XML formatted patient session information in the remote data center database.

43. The system of claim 39, further comprising:

means for transferring the XML formatted patient session information over the Internet to a remote server and storing the XML formatted patient session information in a remote server database accessible by the user employing a web browser;

means for initiating an Internet connection between a user controlled Internet access device operating a web browser; and means for accessing the XML formatted patient session information in the remote server database through the web browser.

44. The system of claim 33, wherein the patient session information is stored in the XML format in IMD memory, and the external medical device further comprises:

means for initiating a telemetry session between an external medical device and the IMD storing patient session information in the XML format; and means for uplink telemetry transmitting the patient session information stored in the IMD in the XML format to the external medical device.

45. The system of claim 44, wherein the external medical device is an IMD programmer.

46. The system of claim 44, wherein the external medical device is an external patient monitor.

47. The system of claim 44, further comprising:

means for transferring the XML formatted patient session information to a remote data center and storing the XML formatted patient session information in a remote data center database accessible by the user; and means for accessing the XML formatted patient session information in the remote data center database.

48. The system of claim 44, further comprising:

means for transferring the XML formatted patient session information over the Internet to a remote server and storing the XML formatted patient session information in a remote server database accessible by the user employing a web browser;

means for initiating an Internet connection between a user controlled Internet access device operating a web browser; and means for accessing the XML formatted patient session information in the remote server database through the web browser.

* * * * *